United States Patent [19]

Fisher

[11] Patent Number: 5,686,286
[45] Date of Patent: Nov. 11, 1997

[54] HPDE IV-C: A NOVEL HUMAN PHOSPHODIESTERASE IV ISOZYME

[75] Inventor: Douglas A. Fisher, Mystic, Conn.

[73] Assignee: Pfizer Inc., New York, N.Y.

[21] Appl. No.: 472,831

[22] Filed: Jun. 7, 1995

Related U.S. Application Data

[60] Division of Ser. No. 286,856, Aug. 5, 1994, which is a continuation-in-part of Ser. No. 112,815, Aug. 25, 1993, abandoned.

[51] Int. Cl.$^6$ .................. C12N 9/20; C12N 9/16; C12N 1/20; C12P 21/06
[52] U.S. Cl. .................. 435/199; 435/196; 435/69.1; 435/252.3; 435/320.1; 536/23.2
[58] Field of Search .................. 435/199, 240.2, 435/196, 320.1, 69.1, 252.3, 172.3; 536/23.2

[56] References Cited

U.S. PATENT DOCUMENTS 5,501,969  3/1996  Hastings et al. .................. 435/252.33
5,504,003  4/1996  Li et al. .................. 435/365.1
5,506,133  4/1996  Yu et al. .................. 435/265

OTHER PUBLICATIONS

Bolger et al. Molecular and Cellular Biology 13(10):6558–6571, Oct. 1, 1993.
Obernolte et al. Gene, 129(2):239–247, Jul. 30, 1993.
Swinnen et al. Proc. Natl. Acad. Sci USA 86:8197–8201, Nov. 1, 1989.

*Primary Examiner*—Robert A. Wax
*Assistant Examiner*—Tekchand Saidha
*Attorney, Agent, or Firm*—Peter C. Richardson; Gregg C. Benson; Robert F. Sheyka

[57] ABSTRACT

This invention relates to a novel nucleic acid sequence encoding a novel human phosphodiesterase IV (hPDE IV) isozyme. It also relates to a polypeptide encoded by such sequence.

This invention also relates to an assay method for detecting the presence of such novel isozyme in human cells, and to a method of identifying compounds or other substances that inhibit or modify the activity of such isozyme.

3 Claims, 3 Drawing Sheets

FIG. 2A

```
-270                                                                                                              -181
        AGATCTCATGTCACACAGGCACTCGGGAACAGATCTGGAACTTGGGTCCAGGAGTCCTGGGTGGCCCCCGTGGAACAGTTTCAGGGT

*  L  P  R  L  P  E↓ D  T
-39                                                                                                                -31
        CCAGATGAAGAGACGAAGTCGCGAGAGAGGCGTGGGGTTGGCAGGCCCCTGACTGCCTCGGCTCCCAG AGGACACG                               -91

G  Q  K  L  A  L  E  T  L  D  E  L  D  W  C  L  D  Q  L  E  T  L  Q  T  R  H  S  V  G  E
-30                                                                                                                 -1
        GGGCAGAAGCTGGCATTGGAGACGCTAGAGCTGGATTGGTGCCTGGATCAGTTGGAGACGCTGCAGACCCGGCACTCGGTGGGGGAG                      -1

M  A  S  N  K  P  K  R  I  L  N  R  E  L  T  H  L  S  G  T  S  R  S  G  N  Q  V  S  E  Y
  1                                                                                                                  30
  1     ATGGCCTCCAACAAGTTCAAGCGGATCCTGAACCGGGAGTTGACCCACCTGTCCGAACCAGCGTCCGGAAACCAGTGTCCGAGTAC                       90

I  S  R  T  F  L  D  Q  Q  T  E  V  E  L  P  K  V  T  A  E  E  A  P  Q  P  M  S  R  I  S
 31                                                                                                                  60
 91     ATCTCCCGGACCTTCCTGGACCAGCAGACCGAGGTGGAGCTGCCCAAGGTGACCGCTGAGGAGGCCCCACAGCCCATGTCCCGATCAGT                    180

G  L  H  G  L  C  H  S  A  S  L  S  S  A  T  V  P  R  F  G  V  Q  T  D  Q  E  E  Q  L  A
 61                                                                                                                  90
181     GGCCTACATGGGCTCTGCCACAGTGCCTCCTCAGCCTCTCCTCCAGCCTGCCACACTGTCCCAGCTTTGGGGTCCAGACTGACCAGGAGGAGCAACTGGCC        270

K  E  L  E  D  T  N  K  W  G  L  D  V  F  K  V  A  E  L  S  G  N  R  P  L  T  A  I  I  F
 91                                                                                                                 120
271     AAGGAGCTAGAAGACACCAACAAGTGGGGACTTGATGTGTTCAAGTGGCGAGCTAAGTGGAACCGGCCCCTCACAGCTATCATATTC                      360

S  I  F  Q  E  R  D  L  L  K  T  F  Q  I  P  A  D  T  L  A  T  Y  L  L  M  L  E  G  H  Y
121                                                                                                                 150
361     AGCATTTTTCAGGAGCGGGACCTGCTGAAGACATTCCAGATACCCGCTGATACCCTGGCACAGACAGACTGGCTACCTGCTGATGCTGGAGGGTCACTAC         450

H  A  N  V  A  Y  H  N  S  L  H  A  A  D  V  A  Q  S  T  H  V  L  L  A  T  P  A  L  E  A
151                                                                                                                 180
451     CACGCCAATGTGGCTACCACAACAGCCTACACAACAGCGCCGACGTGGCCCAGTCCACGCATGTCCTGCTGGCTACGCCCGCCCTCGAGGCT                 540

V  F  T  D  L  E  I  L  A  A  L  F  A  S  A  I  H  D  V  D  H  P  G  V  S  N  Q  F  L  I
181                                                                                                                 210
541     GTGTTCACAGACTTGGAAATCCTGGCTGCCCTCTTTGCAAGCGCCATCCACGACGTGGACCATCCTGGGGTCTCCAACCAGTTTCTGATT                   630

N  T  N  S  E  L  A  L  M  Y  N  D  A  S  V  L  E  N  H  H  L  A  V  G  F  K  L  L  Q  A
211                                                                                                                 240
631     AACACCAACTCAGAGCTGGCGCTTATGTACAACGACGCCTCCGTGCTGGAGAATCATCACCTGGCTGTGGGCTTCAAGCTGCTGCAGGCAGCA                720
```

FIG. 2B

```
241  E  N  C  D  I  F  Q  N  L  S  A  K  Q  R  L  S  L  R  R  M  V  I  D  M  V  L  A  T  D  M   270
721  GAGAACTGCGATATCTTCCAGAACCTCAGCGCCAAGCAGCGACTGAGTCTGCCAGGATGGTCATTGACATGGTGCTGGCCACAGACATG  810

271  S  K  H  M  N  L  L  A  D  L  K  T  M  V  E  T  K  K  V  T  S  L  G  V  L  L  L  D  N  Y   300
811  TCCAAACACATGAACCTCCTGGCCGACCTCAAGACCATGGTGGAGACCAAGAAGGTGACAAGCCTCGGTGTCCTCCTCCTGGACAACTAT  900

301  S  D  R  I  Q  V  L  Q  N  L  V  H  C  A  D  L  S  N  P  T  K  P  L  P  L  Y  R  Q  W  T   330
901  TCCGACCGAATCCAGGTCTTGCAGAATCTGGTGCACTGTGCTGATCTGAGCAACCCTACCAAACCGCTGCCCCTGTACCGCCAGTGGACG  990

331  D  R  I  M  A  E  F  F  Q  Q  G  D  R  E  R  E  S  G  L  D  I  S  P  M  C  D  K  H  T  A   360
991  GACCGCATCATGGCCGAGTTCTTCCAGCAGGGAGACCGCGAGCGTGAGTCGGGCCTGGACATATCAGTCCCATGTGTGACAAGCATACGGCC  1080

361  S  V  E  K  S  Q  V  G  F  I  D  Y  I  A  H  P  L  W  E  T  W  A  D  L  V  H  P  D  A  Q   390
1081 TCAGTGGAGAAGTCCCAGGTGGGTTTCATTGACTACATTGCTCACCCACTGTGGGAGACTTGGGCTGACCTGGTCCACCCAGATGCAACAG  1170

391  D  L  L  D  T  L  E  D  N  R  E  W  Y  Q  S  K  I  P  R  S  P  S  D  L  T  N  P  E  R  D   420
1171 GACCTGCTGGACACGCTGGAGGACAATCGAGAGTGGTACCAGAGCAAGATCCCCCGAAGTCCCTCAGACCTCACCAACCCCGAGCGGGAC  1260

421  G  P  D  R  F  Q  F  E  L  T  L  E  E  A  E  E  E  D  E  E  E  E  G  E  E  T  A  L         450
1261 GGGCCTGACAGATTCCAGTTTGAACTGACTCTGGAGGAGGCAGAGGAGGAAGATGAGGAGGAAGAAGAGGAAGAGGAAGACAGCTTTA     1350

451  A  K  E  A  L  E  L  P  D  T  E  L  L  S  P  E  A  G  P  D  P  G  D  L  P  L  D  N  Q  R   480
1351 GCCAAAGAGGCCCTTGGAGTTGCCTGACACTGAACTCCTGTCCCCTGAAGCCGGCCCAGACCCTGGGGACTTACCCCTGACAACCAGAGG  1440

481  T  *                                                                                       481
1441 ACTTAGGGCCCAGCCCTGCCTGAACTGCAGGGCCAATGGATGGTAAAGCCCTTTGGCTCTTGGCAGGCAGACTTTCCAGGAAGAGGCTCCA  1530
1531 TGTGGCTCCCTGCTTCACTTCCCACCCATTTAGGGAGACAATCAAGCTCTTAGTTATAGGTGGCTCCCAGGTCTAATTGGAGGCACCTG   1620
1621 GCTGGGGTCCACTCTGACCCTAGACTTGCCTAAAAGAGCTCTTAAGGGCAGCCTCTTACGATGCCCTGGTGTCTTTCTCCTGGCTTC     1710
1711 TATCCCTGTGAGAGAGTGCTGTCTGCTGAGCCTCTGAGCCTCCACCCTCTCAGTGTCACTCTTGAGTCACATCTGTCACTTAATTATT    1800
1801 TCCTTCTTTATCAAATATTTA                                                                       1821
```

HPDE IV-C: A NOVEL HUMAN PHOSPHODIESTERASE IV ISOZYME

This is a division of application Ser. No. 08/286,856, filed on Aug. 5, 1994, which is a continuation-in-part of U.S. patent application No. 08/112,815, which was filed on Aug. 25, 1993, now abandoned. U.S. Ser. No. 08/112,815 is incorporated herein by reference in its entirety.

This invention relates to novel nucleic acid sequences encoding a novel human phosphodiesterase IV (hPDE IV) isozyme.

Cyclic nucleotide phosphodiesterases (PDEs) are a family of enzymes that catalyze the degradation cyclic nucleotides. Cyclic nucleotides, particularly cAMP, are important intracellular second messengers, and PDEs are one cellular component that regulates their concentration. In recent years, five PDE enzymes (PDE I–PDE V), as well as many subtypes of these enzymes, have been defined based on substrate affinity and cofactor requirements (Beavo J. A. and Reifsnyder D. H., *Trends Pharmacol. Sci.* 11:150 [1990]; Beavo J., In: *Cyclic Nucleotide Phosphodiesterases: Structure, Regulation and Drug Action*, Beavo J. and Housley M. D. (Eds.). Wiley: Chichester, pp. 3–15 [1990]).

Theophylline, a general PDE inhibitor, has been widely used in the treatment of asthma. It has been speculated that selective inhibitors of PDE isozymes and their subtypes (particularly the cAMP-specific PDE IV) will lead to more effective therapy with fewer side effects (for reviews, see Wieshaar R. E. et al, *J. Med. Chem.*, 28:537 [1985] and Giembycz M. A., *Biochem. Pharm.*, 43:2041 [1992], Lowe J. A. and Cheng J. B., *Drugs of the Future*, 17:799–807 [1992]). However, even PDE IV selective drugs such as rolipram suffer from emetic side effects that limit their use. An even more selective approach is to inhibit individual subtypes of PDE IV, each one of which is expected to have its own tissue distribution. If the PDE IV isozyme responsible for efficacy is different from that causing side effects, an isozyme selective drug could separate therapeutic and side effects. The cloning and expression of the human PDE IVs would greatly aid the discovery of isozyme-selective inhibitors by providing purified isoenzymes to incorporate into drug assays.

Mammalian PDE IV, the homologue of the Drosophila Dunce gene (Chen C. N. et al., *Proc. Nat. Acad. Sci.* (USA) 83:9313 [1986]), is known to have four isoforms in the rat (Swinnen J. V. et al., *Proc. Nat. Acad. Sci.* (USA) 86:5325 [1989]). The cloning of one human isoform of PDE IV from monocytes was reported in 1990 (Livi G. P. et al., *Mol. Cell. Bio.*, 10:2678 [1990]). From Southern blot data, the authors concluded that this enzyme was probably the only PDE IV gene in humans, with the possible exception of one other isozyme. The same group has published the sequence of a second human isoform isolated from brain that they designate hPDE IV-B to distinguish it from the monocyte form, which they designate as hPDE IV-A (McLaughlin M. M. et al., *J. Biol. Chem.* 268:6470 [1993]). We have independently cloned three splice variants of hPDE IV-B, which we have designated hPDE IV-B1, -B2, and -B3. The sequence reported by McLaughlin et al., is nearly identical to our hPDE IV-B2 sequence, while the -B1 and -B3 sequences encode functional PDE IV enzymes with different N-terminal amino acid sequences.

The nucleic acid sequences encoding hPDE IV-B1, hPDE IV-B2 and hPDE IV-B3 are described and claimed in U.S. patent application 08/075,450, which was filed on Jun. 11, 1993. This application is incorporated herein by reference in its entirety.

This invention relates to nucleic acid sequences encoding a novel human PDE IV isozyme, which we designate as hPDE IV-C. Such a novel PDE IV DNA sequence and its encoded peptide may be used to screen for drugs that are selective for the human PDE IV-C isozyme or used to exclude activity against hPDE IV-C to find agents selective for other hPDE IV isozymes. Such novel DNA sequence may also be used in assays to detect the presence of the human PDE IV-C isozyme in human cells, thus providing information regarding the tissue distribution of this isozyme and its biological relevance with respect to particular disease states.

U.S. application Ser. No. 08/122,815, of which this application is a continuation-in-part, claims a hPDE IV-C cDNA sequence containing 1296 base pairs, which encode the C-terminal 306 amino acids of hPDE IV-C. Subsequent to the filing of U.S. application Ser. No. 08/122,815, referred to above, a fragment of the hPDE IV-C cDNA sequence claimed in that application was published by Bolger et. al., *Mol. Cell. Biol.*, 13, 1658 (1993). The fragment published by Bolger et al. is smaller than the sequence claimed in U.S. Ser. No. 08/112,815, and does not encode a large enough portion of the coding region to produce a functional protein. The Bolger sequence constitutes bases 961 to 2091 of SEQUENCE ID NO. 1 of the present invention, and the sequence claimed in U.S. Ser. No. 08/122,815 constitutes bases 796–2091 of SEQUENCE ID NO. 1 of the present invention. SEQUENCE ID NO. 1 of this invention represents a full length hPDE IV-C cDNA sequence which encodes a catalytically active protein that can be used to screen for isozyme selective drugs.

The following abbreviations are used throughout this patent:

| | |
|---|---|
| bp | base pair(s) |
| cAMP | cyclic adenosine 3',5'-monophosphate |
| dNTP | 2'-deoxynucleoside-5'-triphosphate |
| dATP | 2'-deoxyadenosine-5'-triphosphate |
| dCTP | 2'-deoxycytidine-5'-triphosphate |
| dGTP | 2'-deoxyguanine-5'-triphosphate |
| dTTP | 2'-deoxythymidine-5'-triphosphate |
| hPDE IV-A | human monocyte PDE IV |
| hPDE IV-B | human brain PDE IV |
| hPDE IV-B1 | human brain PDE IV, splice variant 1 |
| hPDE IV-B2 | human brain PDE IV, splice variant 2 |
| hPDE IV-B3 | human brain PDE IV, splice variant 3 |
| hPDE IV-C | human testis PDE IV |
| kb | kilobase(s) |
| PCR | polymerase chain reaction |
| PDE | cyclic nucleotide phosphodiesterase |
| PDE I | $Ca^{2+}$/Calmodulin-dependent PDE |
| PDE II | cGMP stimulated PDE |
| PDE III | cGMP inhibited PDE |
| PDE IV | high affinity cAMP-specific PDE |
| PDE V | cGMP specific PDE |
| RACE | Rapid Amplification of cDNA Ends |
| RT | avian myeloblastosis virus (AMV) reverse transcriptase |
| RT-PCR | PCR of RT-transcribed mRNA |
| SSC | 1X SSC = 0.15M NaCl, 0.015 $Na_3$ citrate pH 7.0 |

The nucleotides and amino acids represented in the various sequences contained herein have their usual single letter designations used routinely in the art.

SUMMARY OF THE INVENTION

This invention relates to the full length cDNA sequence of the novel human PDE IV isozyme hPDE IV-C. More specifically, it relates to DNA segments comprising the DNA sequence of SEQUENCE ID NO. 1, as defined below, or an alleleic variation of such sequence. It also relates to polypeptides produced by expression in a host cell into which has been incorporated the foregoing DNA sequence or an alleleic variation thereof.

This invention also relates to an isolated polypeptide containing the amino acid sequence of SEQUENCE ID NO. 2 or SEQUENCE ID NO. 3.

This invention also relates to recombinant DNA comprising the DNA sequence of SEQUENCE ID NO. 1, or an alleleic variation thereof.

This invention also relates to an isolated DNA segment comprising the genomic promoter region that regulates transcription or translation of the DNA sequence of SEQUENCE ID NO. 1, or an allelic variation thereof.

This invention also relates to an assay method for detecting the presence of hPDE IV-C in human cells comprising: (a) performing a reverse transcriptase-polymerase chain reaction on total RNA from such cells using a pair of polymerase chain reaction primers that are specific for hPDE IV-C, as determined from the DNA sequence of SEQUENCE ID NO. 1, or an allelic variation thereof; and (b) assaying the appearance of a appropriately sized PCR fragment by agarose gel electrophoresis.

This invention also relates to a method of identifying compounds or other substances that inhibit or modify the activity of hPDE IV-C, comprising measuring the activity of hPDE IV-C in: (a) a cell line into which has been incorporated recombinant DNA comprising the DNA sequence of SEQUENCE ID NO. 1, or an alleleic variation thereof, or (b) a cell population or cell line that naturally selectively expresses hPDE IV-C, as determined by the assay method described above.

This invention also relates to an isolated DNA segment comprising a DNA sequence that is a subset of SEQUENCE ID NO. 1, or an alleleic variation thereof, and that is capable of hybridizing to SEQUENCE ID NO. 1, or an alleleic variation thereof, when used as a probe, or of amplifying all or part of such sequence when used as a polymerase chain reaction primer.

As used herein, the term "functionally equivalent DNA segment" refers to a DNA segment that encodes a polypeptide having an activity that is substantially the same as the activity of the polypeptide encoded by the DNA to which such segment is said to be functionally equivalent.

As used herein, the term "subset of a DNA sequence" refers to a nucleotide sequence that is contained in an represents part, but not all of such DNA sequence, and is sufficient to render it specific to such sequence when used as a PCR primer and render it capable of hybridizing to such sequence when used as a probe at high stringency.

As used herein, the term "functionally equivalent polypeptide" refers to a polypeptide that has substantially the same activity as the polypeptide to which it is said to be functionally equivalent.

As used herein, the term "subset of a polypeptide" refers to a peptide sequence that is contained in and represents part, but not all of such polypeptide.

BRIEF DESCRIPTION OF THE DRAWINGS

FIG. 2. hPDE IV-C DNA Sequence and Translated Amino Acid Sequence. The translated amino acids of hPDE IV-C are indicated above the cDNA sequence. The stop codon (bp 1,444–1,446) is indicated by "Trm". Positive numbering begins at the putative start codon with negative numbering (cDNA and amino acids) back into the 5' UTR. A putative splice junction is indicated by an arrow at nucleotide (nt) −99, the homologous position seen in hPDE IV-B. An in frame stop codon (nt −117 to −115) in the 5' UTR is noted by an asterisk. The sequence claimed in U.S. Ser. No. 08/122,815 begins at nt 526 (796 in SEQUENCE ID NO. 1), amino acid (AA) 176, and continues to the end of the sequence. There are three changes in the nucleotide sequence from the parent case (U.S. Ser. No. 08/112,815). These are the following (using the numbering from SEQ. ID NO. 1 of U.S. Ser. No. 08/112,815): nt 3 changes from C to G, nt 7 changes from T to C, and nt 438 changes from A to G. One of these (nt 7) changes an amino acid, so amino acid 3 of SEQ. ID NO. 2 of U.S. Ser. No. 08/122,815 is changed from Phe to Leu. The corresponding positions of these changes in the present application are: (SEQUENCE ID NO. 1—nt 798, 802, and 1,233; SEQUENCE ID NO. 2—AA 178; SEQUENCE ID NO. 3—AA 203).

DETAILED DESCRIPTION OF THE INVENTION

Figure 1:
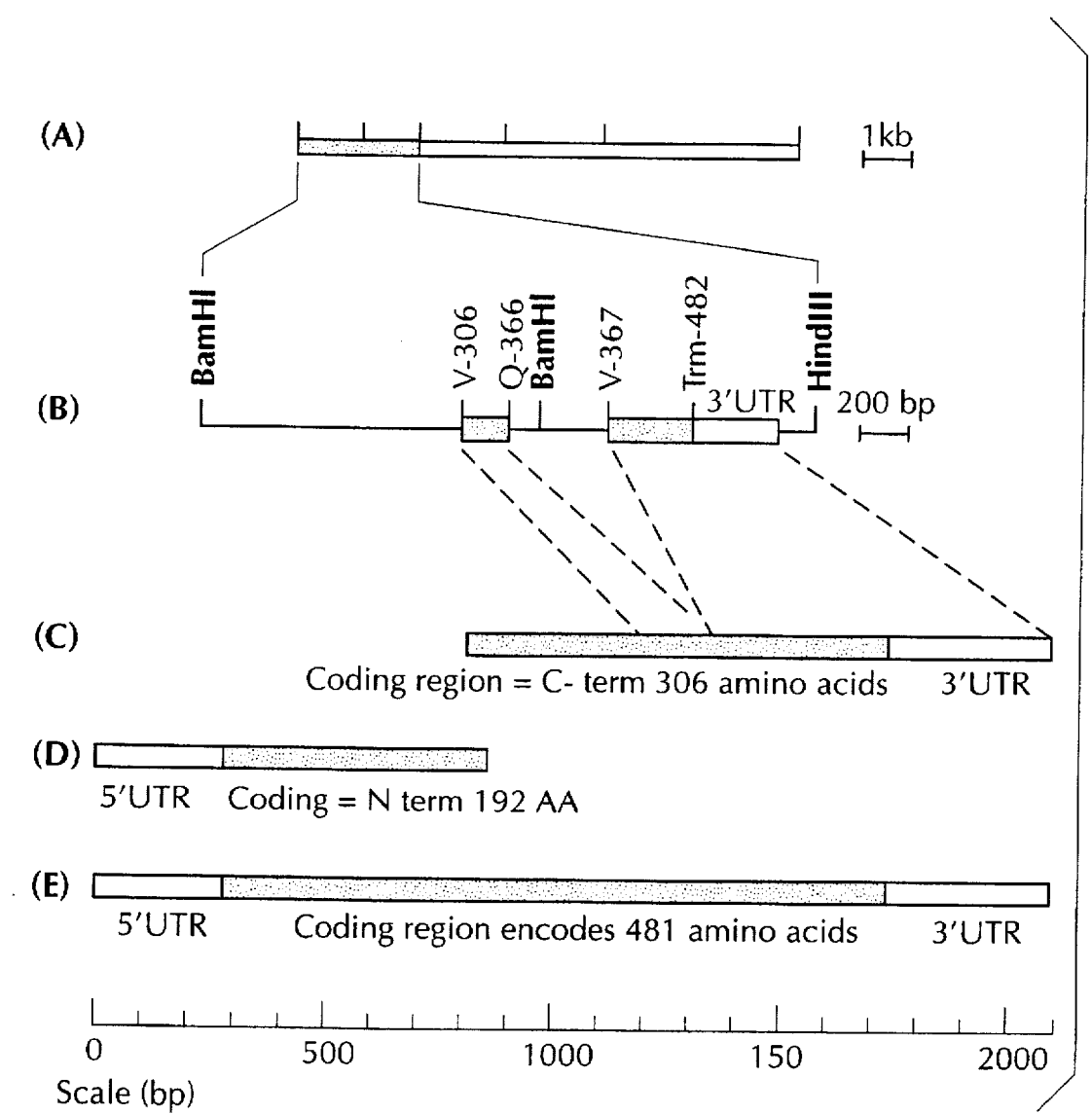
FIG. 1. hPDE IV-C Restriction Map and Clone Diagram. (A) Partial restriction map of the approximately 11 kb insert of clone λC2.1, the genomic clone containing two exons of hPDE IV-C. The region hybridizing with the hPDE IV-A,B probes is indicated as a shaded box. (B) Diagram of the 2.7 kb of DNA indicated by a shaded box in (A). Protein coding exons are indicated by solid boxes, while the 3' untranslated region (3'UTR) is indicated as an open box. The amino acids at the intron exon boundaries (numbering as in FIG. 2) are shown above the solid boxes. The 3'UTR is only indicated as far as was confirmed by the cDNA clone of hPDE IV-C, T.29. It is not known if the 3'UTR extends further in the 3' direction on λC2.1. (C) Diagram of the insert of cDNA clone T.29, a cDNA clone containing a partial hPDE IV sequence. Solid boxes indicated protein coding regions, while open boxes indicate 3'UTR. Dashed lines from (B) show the regions in (C) corresponding to the exons in (B). (D) Diagram of the region cloned by 5' RACE, which encodes the N-terminal 192 amino acids (solid box) and 270 bp of 5' untranslated region (open box). (E) Diagram of the assembled full length cDNA sequence encoding a 481 amino acid polypeptide. Scale at the bottom relates to (C),(D), and (E). Scales for (A) and (B) are to the right of each diagram.

The procedures by which the DNA sequence encoding the novel isozyme, hPDE IV-C, was identified and isolated are described below.

DISCOVERY OF hPDE IV-C BY ISOLATION OF A GENOMIC CLONE

A human genomic library was screened as described in Materials and Methods, and clone λC2.1 was isolated. A partial restriction map of the approximately 11 kb insert is shown in FIG. 1A. Only the region indicated by the shaded box in FIG. 1A hybridized to the hPDE IV-A,B probe, and the DNA sequence of this region was determined.

Two exons with homology (85–95%) to known PDE IV genes were found (FIG. 1B, solid boxes) in the region sequenced. This level of homology clearly places this gene in the PDE IV gene family. Since this gene is not identical to either of the known human PDE IV genes, we conclude that this is a novel human PDE IV gone, and designate it as hPDE IV-C. Together, these two exons of hPDE IV-C would encode the C-terminal 176 amino acids of a hPDE IV protein. The exact extent of the 3' untranslated region is unclear, because this region is not conserved in homologous genes and because it is possible that there is an intron in the 3'UTR. The 176 amino acids extend 94 amino acids into the highly conserved approximately 270 amino acid catalytic domain of PDE IV (Swinnen J. V. et al., *Proc. Nat. Acad. Sci.* (USA) 86:5325 [1989]).

ISOLATION OF A cDNA CLONE FOR hPDE IV-C

A human testis cDNA library was screened as described in Materials and Methods, and cDNA clone T.29 was obtained. The DNA sequence of the insert was determined, and is shown in SEQUENCE ID NO. 1 and in FIG. 2, with the exception of 33 bp of a likely cloning artifact at the 5' end. A diagram of clone T.29 and its relationship to the two exons determined for clone λC2.1 are shown in FIG. 1C. The 3' 906 bp (bp 1186–2091 in SEQUENCE ID NO. 1) of clone T.29 are identical to the sequence determined from clone λC2.1. The sequence of T.29 extends the sequence of hPDE IV-C another 390 bp in the 5' direction (bp 796–1185 in SEQUENCE ID NO.1, FIG. 2), adding 130 amino acids to the amino acid sequence, or 224 amino acids into the approximately 270 amino acid catalytic domain. This means that T.29 is not full length and encodes the C-terminal 306 amino acids of hPDE IV-C.

Since no polyA tract was found at the 3' end of clone T.29, and since the cDNA library was made by a combination of oligo dT and random priming, we do not believe that the 3' untranslated region is full length. However, this is probably of no functional significance with respect to producing a recombinant PDE since this region does not encode protein.

COMPLETION OF A FULL LENGTH cDNA USING 5' RACE

5' RACE was performed as described below in Materials and Methods, section (e). The hPDE IV-C cDNA sequence was extended farther 5', as shown In FIG. 1D. The combined cDNA sequence (FIG. 1E) contains a full length cDNA of one splice variant. The predicted amino acid sequence is 481 amino acids in length. Clearly, there are other splice variants, because the region upstream of the start codon (AA's −1 to −33 in FIG. 2) has homology to other PDE IV genes, and this similarity terminates precisely at the point homologous to a splice junction in hPDE IV-B (shown by an arrow in FIG. 2). For nucleotides −1 to −98 to be conserved in evolution, they must be protein codins in another splice variant, so other N-terminally extended variants must exist. Such variants have not yet been cloned, but further 5' RACE experiments in multiple tissues could elucidate these variants.

The translated amino acid sequence of hPDE IV-C is most similar to the rat PDE IV isozyme PDEI (Swinnen J. V. et al., [1989]) with 92.5% identity in the 267 amino acids of the catalytic domain. The rat PDE 2, 3 and 4 isozymes referred to in that reference have 88.0%, 88.4%, and 85.8% amino acid identity, respectively, over the same region. The present inventor tentatively identifies hPDE IV-C as the human homolog of the rat PDE IV isozyme PDEI. The other human isozymes are approximately as different from hPDE IV-C as hPDE IV-C is from the rat isozymes; with hPDE IV-A and hPDE IV-B sharing 88.8% and 86.1% amino acid identity in the catalytic domain.

hPDE IV-C IS EXPRESSED IN HUMAN BRAINSTEM

The fact that a clone for hPDE IV-C was isolated from a testis cDNA library shows that this gene is expressed in the testis and processed into polyA+mRNA. To further show that hPDE IV-C is expressed, we analyzed human tissues by RT-PCR using the methods described in Materials and Methods and the hPDE IV-C specific PCR primer pairs described below in Assays. hPDE IV-C is expressed in a number of tissues, with the highest levels occurring in the brain.

EXPRESSION CLONING OF hPDE IV-C

The hPDE IV-C cDNA sequence was cloned into pcDNA8 (Invitrogen) for expression in mammalian cells. Since the region encoding 33 amino acids upstream of the putative start codon is likely used in other splice variants, we added some of these amino acids in making an expression construct. In hPDE IV-B3 (Fisher, D. A. and Robbins, M. D., U.S. Ser. No. 08/075,450, referred to above), a methionine at the homologous position to leucine −25 serves as a functional start codon that makes a catalytically active protein. Therefore, we mutated leu −25 into a met start codon, added translation initiation sequences (Kozak, M., *Nucleic Acids Res.*, 15:8125 [1987]), and cloned into pcDNA3 to produce the plasmid pc3-hPDE IV-C. Because of the addition of a Kpnl restriction site to the sequence, the first three amino acids are altered. The expression construct is predicted to make the polypeptide shown in SEQUENCE ID NO. 3.

After transient transfection into 293 cells by methods familiar to those skilled in the art (calcium phosphate precipitation, electroporation, etc.) the expression construct leads to the synthesis of catalytically active hPDE IV-C, as evidenced by a 3–10× increase in PDE IV enzymatic activity over pcDNA3 (vector) transfected controls. Therefore, the disclosed sequence is sufficient to produce functional hPDE IV-C. The expression construct pc3-hPDE IV-C has been deposited with the ATCC (see below).

DEPOSITS

The cDNA expression clone containing the hPDE IV-C sequence, pc3-hPDE IV-C, has been deposited with the American Type Culture Collection, Rockville, Md. U.S.A. (ATCC) and assigned the accession number ATCC 69609.

ASSAYS

Using the DNA sequence of hPDE IV-C, hPDE IV-B, and hPDE IV-A, one skilled in the art could make a large number of isoenzyme specific PCR primer pairs. Specificity is achieved by choosing primers that are an exact match for the desired isozyme but which have enough mismatches in the homologous region of the undesired isozymes to render them incapable of amplifying a DNA fragment from mRNA from those isozymes in an RT-PCR assay. We have made and tested the following hPDE IV-C, hPDE IV-B, and hPDE IV-A specific primer pairs. The primers 5'C (5'-GGAGAAGTCCCAGGTGGGTTT-3') and 3'C (5'-TCTGGTTGTCGAGGGGTAAGT-3') are a pair of 21-mers that specifically amplify a 350 bp fragment of hPDE IV-C. The primers 5'B (5'-CGAAGAAGTTACAAGTTC-3') and 3'B (5'-AACCTGGGATTTTTCCACA-3') are a pair of 19-mers that specifically amplify a 245 bp fragment from hPDE IV-B. The primers 5'A (5'-CACCTGCATCATGTACATG-3') and 3'A (5'-TCCCGGTTGTCCTCCAAAG-3') are 19-mers that amplify an 850 bp fragment specifically from hPDE IV-A. Using these primers, one can sensitively assay the presence of these three isozymes in any tissue from which total RNA can be isolated (e.g., by the method of Chomcynski P. and N. Sacchi, *Anal. Biochem.* 162:156 [1987]) by performing an RT-PCR reaction on such RNA using the specific primers and then assaying the amount of the appropriately sized DNA PCR product by agarose gel electrophoresis. The RT-PCR conditions are identical to those described in Materials and Methods.

The claimed DNA sequences of this invention can be reproduced by one skilled in the art by either PCR amplification from brainstem RNA using PCR primers designed from the sequences, or by obtaining the described cDNA clone directly from ATCC. The promoter regions can be isolated from a genomic library, using the claimed sequences as probes.

UTILITY OF THE INVENTION

A general utility of the novel human PDE IV genes and their encoded peptides is to allow screening for human PDE IV isozyme specific/selective drugs that may be improved therapeutics in the areas of asthma and inflammation. The cloned genes make it possible, by expression cloning methods familiar to those skilled in the art, to produce active, purified isoenzymes that can be used in PDE IV activity assays (e.g., Davis C. W., and Daly J. W., *J. Cyclic Nucleotide Res.* 5:65 [1979], Torphy T. J. and Cielinski L. B., *Mol. Pharm.* 37:206 [1990]) to measure the potency of inhibitors against individual isoenzymes.

Genomic sequences are also of utility in the context of drug discovery. It may be valuable to inhibit the mRNA transcription of a particular isoform rather than to inhibit its translated protein. This is particularly true with hPDE IV-B, since the different splice variants may be transcribed from different promoters. There is precedent for multiple promoters directing the transcription of a mouse brain 2',3'-cyclic-nucleotide 3' phosphodiesterase (Kurihara T. et al., *Biochem. Biophys. Res. Comm.* 170:1074 [1990]). This invention would provide the means for one skilled in the art to locate the promoter of hPDE IV-C. After isolating a full length cDNA clone using the hPDE IV-C sequence as a probe, screening of a human genomic library with the 5' cDNA sequences should allow isolation of genomic clones containing the promoter. Such promoters could then be linked to a convenient reporter gene such as firefly luciferase (de Wet J. R. et al., *Mol. Cell. Biol.* 7:725 [1987]), transfected into a mammalian cell line, and agents screened for that inhibit the activity of the promoter of interest while having minimal effect on other promoters.

Another utility of the invention is that the DNA sequences, once known, give the information needed to design assays to specifically detect each isoenzyme or splice variant. Isozyme-specific PCR primer pairs are but one example of an assay that depends completely on the knowledge of the specific DNA sequence of the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific hPDE IV isozymes are shown to associated with a particular disease state, the invention would be valuable in the design of diagnostic assays to detect the presence of isozyme mRNA.

MATERIALS AND METHODS

(a) Cells/Reagents

Human brainstem tissue was purchased from the International Institute for the Advancement of Medicine. Unless noted below, all restriction endonucleases and DNA modifying enzymes were from Boehringer-Mannheim.

(b) RT-PCB

Total RNA was isolated from human tissue as previously described (Chomcynski P. and Sacchi N., *Anal. Biochem.* 162:156 [1987]). To prepare an 80 μl reverse transcriptase (RT) reaction, 4 μg total RNA and 4 μg random hexamer primers (Pharmacia/LKB) were heated to 90° C. for 5 min in 60 μl RNase free water. After chilling on ice, the reaction was brought to 80 μl and the following conditions by the addition of concentrated stocks: 1X RT buffer (50 mM Tris pH 8.3, 6 mM magnesium chloride ($MgCl_2$) 40 mM potassium chloride (KCl); 1 mM each dATP, dGTP, dCTP, and dTTP; 1 mM dithiothreitol; 25 U/ml RNasin (Promega); and 900 U/ml AMV reverse transcriptase (RT). Incubate at 42° C. for 1 hour, then boil for 5 min to kill the RT.

A 50 μl PCR reaction was set up by using 3.25 μl of the above reaction mix. Final buffer conditions were (including carryover from RT): 10 mM Tris pH 8.3, 50 mM potassium chloride (KCl), 1.5 mM $MgCl_2$, 10 μg/ml bovine serum albumin, 2.5% (v/v) Formamide, 200 μM ea dNTP, 0.5 pmol/μl each degenerate primer, and 0.05 U/μl Amplitaq polymerase (Perkin Elmer). Amplification was done in a Perkin Elmer 9600 PCR thermocycler using the following parameters: Denature-94° C., 30 sec; Anneal-55° C., 30 sec, Polymerize-72° C., 60 sec. Amplify for 35 cycles.

(c) Library Screening $1 \times 10^6$ clones from a commercially available human genomic library (Clontech #HL1111j) were screened with a 308 bp PCR fragment of hPDE IV-A from the highly conserved PDE catalytic domain (bp 1069 to 1376 [amino acids 357–459] in Livi G. P. et al., [1990]) and the homologous fragment from hPDE IV-B. The screening conditions were as follows: 5X SSC, 5X Denhardts solution (1X Denhardt's=0.02% each of Ficoll, polyvinylpyrrolidone, and bovine serum albumin), 40% formamide, 0.5% sodium dodecyl sulfate, and 20 μg/ml herring sperm DNA. Probe concentration was $4 \times 10^5$ cpm/ml. The filters were hybridized at 42° C. for >16 hours, and then washed to a final stringency of 0.5 X SSC at room temperature.

$1 \times 10^5$ clones from a human testis cDNA library (Clontech: HL1161a) were screened as for the genomic library, except the formamide concentration was 35%. The filters were washed to a final stringency of 0.5 X SSC at room temperature.

(d) DNA Sequencing

All DNA sequencing was done using an ABI model 373A DNA sequencer on DNA fragments cloned into various pGEM vectors (Promega). Sequencing reactions were done using the Taq sequencing method.

(e) RACE Method

The RACE method (Rapid Amplification of cDNA Ends) was adapted from a published method (Frohman M. A. and Martin G. R., In: *Technique—a Journal of Methods in Cell and Molecular Biology*, Vol. 1, NO. 3, pp. 165–170 [1989]). Three nested gene-specific primers described in the above reference (GS-RT, GSo, and GSi) need to be designed for each gene to be amplified. The following conditions were used successfully for hPDE IV-C: In order to produce the 5' end of a hPDE IV cDNA, an RT reaction was performed on brainstem total RNA as above with the exception that the gene specific RT primer (GS-RT:5'-AGCCAGGTGATGATT-3') was at a concentration of 0.1 pmol/μl. The reaction is incubated at 42° C. for 1 hour and then shifted to 52° C. for 30 min. (This higher temperature seemed to be critical to avoiding a premature truncation product in hPDE IV-B, presumably because of a sequence that RT has difficulty reading through, and this was adopted for hPDE IV-C as well.)

After removing buffers using a Centricon 30 filtration device and concentrating in a speedvac, one tails the cDNA with dATP using terminal transferase (TdT) in a 20 µl reaction volume. Final conditions are: 1×TdT buffer (40 mM potassium cacodylate pH 6.8, 0.1 mM dithiothreitol), 0.75 mM cobalt chloride (CoCl$_2$), 0.2 mM dATP, 1,250 U TdT/ ml. Incubate 37° C. for 5 min, inactivate TdT at 65° C. 5 min. This reaction is diluted with water to 500 µl and used as a template in a series of nested PCR reactions.

The first PCR amplification (50 µl) uses the same PCR buffer conditions as above, but uses three primers: the Primer/Adapter (Ro-Ri-dT$_{17}$ 5'-AAGCATCCGTCAGCATCGGCAGGACAAC(T$_{17}$)-3') at 0.2 pmol/µl, the Forward Outside Primer (Ro: 5'-AAGCATCCGTCAGCATC-3') at 0.5 pmol/µl, and the Gene-Specific Reverse Outside Primer (GSo: 5'-ACCGAGGCGTCGTTGTA-3') at 0.5 pmol/µl. Taq polymerase is only added after denaturing the reaction to 95° C. for 5 min. and equilibrating to 72° C. For the first cycle, the annealing step is 10 min. at 55° C., and the extension is at 72° C. for 40 min. After that, cycling parameters (PE 9600 machine) are: Denature 94° C., 30 sec; Anneal 53° C., 30 sec; Polymerize 72° C., 45 sec. Amplify 28 cycles. Dilute this product 20× in water to serve as template for a second PCR reaction using primers nested just inside those used in the first PCR reaction. This greatly increases the specificity of the final PCR products.

The second 50 µl PCR reaction uses identical buffer conditions to the first, and uses 1 µl of the 20× diluted product from the first PCR reaction. The primers are the Forward Inside Primer (Ri: 5'-AGCATCGGCAGGACAAC-3') and Gene-Specific Inside Primer (GSi: 5'-AAGAGGGCAGCCAGGAT-3'), both at 0.5 pmol/µl. For 12 cycles, the parameters are the same as the final 28 cycles of the previous amplification. The annealing temperature is then raised to 60° C. for another 18 cycles. Products are then analyzed on an agarose gel. DNA fragments are gel isolated, subcloned into a convenient vector, and sequenced. DNA fragments should extend from the GSi primer to the 5' end of the mRNA(s). After obtaining a 5' sequence, this sequence is verified by re-amplifying it from cDNA (two independent PCR reactions) using unique primers designed from the sequence and resequencing the fragments obtained.

SEQUENCE ID SUMMARY 1. hPDE IV-C cDNA sequence. 2,091 bp.

2. Predicted amino acid sequence of hPDE IV-C. 481 amino acids.

3. Predicted amino acid sequence encoded by the hPDE IV-C expression vector pc3-hPDE IV-C. 506 amio acids.

I claim:

1. A purified polypeptide containing the amino acid sequence of SEQ ID NO: 2 or SEQ ID NO: 3.

2. A polypeptide that shows at least 95% sequence homology to a polypeptide according to claim 1.

3. A polypeptide produced by the expression in a host cell into which has been incorporated the DNA sequence of SEQ ID NO: 1.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2091 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AGATCTCATG   GTCACACAGG   CACTCGGGGA   ACAGATCTGG   AACTTGGGTC   CAGGAGTCCT        60

GGGTGGCCCC   CGTGGGAACA   GTTTCAGGGT   CCAGATGAAG   AGACGAAGTC   GCGAGAGGCG       120

TGGGGTCCCT   GAGCGGGGGG   TTGGGCAGGC   CCCTGACTGC   CTCGGCTCCC   AGAGGACACG       180

GGGCAGAAGC   TGGCATTGGA   GACGCTAGAC   GAGCTGGACT   GGTGCCTGGA   TCAGTTGGAG       240

ACGCTGCAGA   CCCGGCACTC   GGTGGGGGAG   ATGGCCTCCA   ACAAGTTCAA   GCGGATCCTG       300

AACCGGGAGT   TGACCCACCT   GTCCGAAACC   AGCCGCTCCG   GGAACCAGGT   GTCCGAGTAC       360

ATCTCCCGGA   CCTTCCTGGA   CCAGCAGACC   GAGGTGGAGC   TGCCCAAGGT   GACCGCTGAG       420

GAGGCCCCAC   AGCCCATGTC   CCGGATCAGT   GGCCTACATG   GGCTCTGCCA   CAGTGCCAGC       480

CTCTCCTCAG   CCACTGTCCC   ACGCTTTGGG   GTCCAGACTG   ACCAGGAGGA   GCAACTGGCC       540

AAGGAGCTAG   AAGACACCAA   CAAGTGGGGA   CTTGATGTGT   TCAAGGTGGC   GGAGCTAAGT       600

GGGAACCGGC   CCCTCACAGC   TATCATATTC   AGCATTTTTC   AGGAGCGGGA   CCTGCTGAAG       660
```

| | | | | | |
|---|---|---|---|---|---|
| ACATTCCAGA | TCCCAGCAGA | CACACTGGCC | ACCTACCTGC | TGATGCTGGA | GGGTCACTAC | 720 |
| CACGCCAATG | TGGCCTACCA | CAACAGCCTA | CATGCCGCCG | ACGTGGCCCA | GTCCACGCAT | 780 |
| GTGCTGCTGG | CTACGCCGGC | CCTCGAGGCT | GTGTTCACAG | ACTTGGAAAT | CCTGGCTGCC | 840 |
| CTCTTTGCAA | GCGCCATCCA | CGACGTGGAC | CATCCTGGGG | TCTCCAACCA | GTTTCTGATT | 900 |
| AACACCAACT | CAGAGCTGGC | GCTTATGTAC | AACGACGCCT | CGGTGCTGGA | GAATCATCAC | 960 |
| CTGGCTGTGG | GCTTCAAGCT | GCTGCAGGCA | GAGAACTGCG | ATATCTTCCA | GAACCTCAGC | 1020 |
| GCCAAGCAGC | GACTGAGTCT | GCGCAGGATG | GTCATTGACA | TGGTGCTGGC | CACAGACATG | 1080 |
| TCCAAACACA | TGAACCTCCT | GGCCGACCTC | AAGACCATGG | TGGAGACCAA | GAAGGTGACA | 1140 |
| AGCCTCGGTG | TCCTCCTCCT | GGACAACTAT | TCCGACCGAA | TCCAGGTCTT | GCAGAACCTG | 1200 |
| GTGCACTGTG | CTGATCTGAG | CAACCCCACC | AAGCCGCTGC | CCTGTACCG | CCAGTGGACG | 1260 |
| GACCGCATCA | TGGCCGAGTT | CTTCCAGCAG | GGAGACCGCG | AGCGTGAGTC | GGGCCTGGAC | 1320 |
| ATCAGTCCCA | TGTGTGACAA | GCATACGGCC | TCAGTGGAGA | AGTCCCAGGT | GGGTTTCATT | 1380 |
| GACTACATTG | CTCACCCACT | GTGGGAGACT | TGGGCTGACC | TGGTCCACCC | AGATGCACAG | 1440 |
| GACCTGCTGG | ACACGCTGGA | GGACAATCGA | GAGTGGTACC | AGAGCAAGAT | CCCCCGAAGT | 1500 |
| CCCTCAGACC | TCACCAACCC | CGAGCGGGAC | GGGCCTGACA | GATTCCAGTT | TGAACTGACT | 1560 |
| CTGGAGGAGG | CAGAGGAAGA | GGATGAGGAG | GAAGAAGAGG | AGGGGGAAGA | GACAGCTTTA | 1620 |
| GCCAAAGAGG | CCTTGGAGTT | GCCTGACACT | GAACTCCTGT | CCCTGAAGC | CGGCCCAGAC | 1680 |
| CCTGGGGACT | TACCCCTCGA | CAACCAGAGG | ACTTAGGGCC | AGCCTGCGT | GAACTGCAGG | 1740 |
| GCCAATGGAT | GGTAAAGCCC | TTTGGCTCTT | GGCAGGCAGA | CTTTCCAGGA | AGAGGCTCCA | 1800 |
| TGTGGCTCCT | GCTTCACTTT | CCCACCCATT | TAGGGAGACA | ATCAAGCTCT | TAGTTATAGG | 1860 |
| TGGCTCCCAG | GGTCTAATTG | GAGGCACCTG | GCTGGGGTCC | ACTCTGACCC | TAGACTTGCC | 1920 |
| TAAAAGAGCT | CTCTAAGGGG | CAGCCTCTTA | CGATGCCCTG | GTGTCTTTCT | CCTGGGCTTC | 1980 |
| TATCCCTGTG | AGGAGAGGTG | CTGTCTGCTG | GAGCCTCTAG | TCCACCCTCT | CCAGTGGTCA | 2040 |
| CTCTTGAGTC | ACATCTGTCA | CTTAATTATT | TCCTTCTTTA | TCAAATATTT | A | 2091 |

( 2 ) INFORMATION FOR SEQ ID NO:2:

( i ) SEQUENCE CHARACTERISTICS:
( A ) LENGTH: 481 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

| Met | Ala | Ser | Asn | Lys | Phe | Lys | Arg | Ile | Leu | Asn | Arg | Glu | Leu | Thr | His |
|---|---|---|---|---|---|---|---|---|---|---|---|---|---|---|---|
| 1 | | | | 5 | | | | | 10 | | | | | 15 | |

| Leu | Ser | Glu | Thr | Ser | Arg | Ser | Gly | Asn | Gln | Val | Ser | Glu | Tyr | Ile | Ser |
|---|---|---|---|---|---|---|---|---|---|---|---|---|---|---|---|
| | | | 20 | | | | | 25 | | | | | 30 | | |

| Arg | Thr | Phe | Leu | Asp | Gln | Gln | Thr | Glu | Val | Glu | Leu | Pro | Lys | Val | Thr |
|---|---|---|---|---|---|---|---|---|---|---|---|---|---|---|---|
| | | | 35 | | | | | 40 | | | | | 45 | | |

| Ala | Glu | Glu | Ala | Pro | Gln | Pro | Met | Ser | Arg | Ile | Ser | Gly | Leu | His | Gly |
|---|---|---|---|---|---|---|---|---|---|---|---|---|---|---|---|
| | 50 | | | | | 55 | | | | | 60 | | | | |

| Leu | Cys | His | Ser | Ala | Ser | Leu | Ser | Ser | Ala | Thr | Val | Pro | Arg | Phe | Gly |
|---|---|---|---|---|---|---|---|---|---|---|---|---|---|---|---|
| 65 | | | | | 70 | | | | | 75 | | | | | 80 |

| Val | Gln | Thr | Asp | Gln | Glu | Glu | Gln | Leu | Ala | Lys | Glu | Leu | Glu | Asp | Thr |
|---|---|---|---|---|---|---|---|---|---|---|---|---|---|---|---|
| | | | | 85 | | | | | 90 | | | | | 95 | |

| Asn | Lys | Trp | Gly | Leu | Asp | Val | Phe | Lys | Val | Ala | Glu | Leu | Ser | Gly | Asn |
|---|---|---|---|---|---|---|---|---|---|---|---|---|---|---|---|

|   |   |   | 100 |   |   |   |   | 105 |   |   |   |   | 110 |   |   |
|---|---|---|---|---|---|---|---|---|---|---|---|---|---|---|---|
| Arg | Pro | Leu | Thr | Ala | Ile | Ile | Phe | Ser | Ile | Phe | Gln | Glu | Arg | Asp | Leu |
|   |   |   | 115 |   |   |   |   | 120 |   |   |   |   | 125 |   |   |
| Leu | Lys | Thr | Phe | Gln | Ile | Pro | Ala | Asp | Thr | Leu | Ala | Thr | Tyr | Leu | Leu |
|   |   |   | 130 |   |   |   |   | 135 |   |   |   |   | 140 |   |   |
| Met | Leu | Glu | Gly | His | Tyr | His | Ala | Asn | Val | Ala | Tyr | His | Asn | Ser | Leu |
|   |   |   | 145 |   |   |   |   | 150 |   |   |   |   | 155 |   | 160 |
| His | Ala | Ala | Asp | Val | Ala | Gln | Ser | Thr | His | Val | Leu | Leu | Ala | Thr | Pro |
|   |   |   |   | 165 |   |   |   |   |   | 170 |   |   |   | 175 |   |
| Ala | Leu | Glu | Ala | Val | Phe | Thr | Asp | Leu | Glu | Ile | Leu | Ala | Ala | Leu | Phe |
|   |   |   | 180 |   |   |   |   | 185 |   |   |   |   | 190 |   |   |
| Ala | Ser | Ala | Ile | His | Asp | Val | Asp | His | Pro | Gly | Val | Ser | Asn | Gln | Phe |
|   |   | 195 |   |   |   |   | 200 |   |   |   |   | 205 |   |   |   |
| Leu | Ile | Asn | Thr | Asn | Ser | Glu | Leu | Ala | Leu | Met | Tyr | Asn | Asp | Ala | Ser |
|   | 210 |   |   |   |   | 215 |   |   |   |   | 220 |   |   |   |   |
| Val | Leu | Glu | Asn | His | His | Leu | Ala | Val | Gly | Phe | Lys | Leu | Leu | Gln | Ala |
| 225 |   |   |   |   | 230 |   |   |   |   | 235 |   |   |   |   | 240 |
| Glu | Asn | Cys | Asp | Ile | Phe | Gln | Asn | Leu | Ser | Ala | Lys | Gln | Arg | Leu | Ser |
|   |   |   |   | 245 |   |   |   |   | 250 |   |   |   |   | 255 |   |
| Leu | Arg | Arg | Met | Val | Ile | Asp | Met | Val | Leu | Ala | Thr | Asp | Met | Ser | Lys |
|   |   |   | 260 |   |   |   |   | 265 |   |   |   |   | 270 |   |   |
| His | Met | Asn | Leu | Leu | Ala | Asp | Leu | Lys | Thr | Met | Val | Glu | Thr | Lys | Lys |
|   |   | 275 |   |   |   |   | 280 |   |   |   |   | 285 |   |   |   |
| Val | Thr | Ser | Leu | Gly | Val | Leu | Leu | Leu | Asp | Asn | Tyr | Ser | Asp | Arg | Ile |
|   |   | 290 |   |   |   |   | 295 |   |   |   |   | 300 |   |   |   |
| Gln | Val | Leu | Gln | Asn | Leu | Val | His | Cys | Ala | Asp | Leu | Ser | Asn | Pro | Thr |
| 305 |   |   |   |   | 310 |   |   |   |   | 315 |   |   |   |   | 320 |
| Lys | Pro | Leu | Pro | Leu | Tyr | Arg | Gln | Trp | Thr | Asp | Arg | Ile | Met | Ala | Glu |
|   |   |   |   | 325 |   |   |   |   | 330 |   |   |   |   | 335 |   |
| Phe | Phe | Gln | Gln | Gly | Asp | Arg | Glu | Arg | Glu | Ser | Gly | Leu | Asp | Ile | Ser |
|   |   |   | 340 |   |   |   |   | 345 |   |   |   |   | 350 |   |   |
| Pro | Met | Cys | Asp | Lys | His | Thr | Ala | Ser | Val | Glu | Lys | Ser | Gln | Val | Gly |
|   |   | 355 |   |   |   |   | 360 |   |   |   |   | 365 |   |   |   |
| Phe | Ile | Asp | Tyr | Ile | Ala | His | Pro | Leu | Trp | Glu | Thr | Trp | Ala | Asp | Leu |
|   | 370 |   |   |   |   | 375 |   |   |   |   | 380 |   |   |   |   |
| Val | His | Pro | Asp | Ala | Gln | Asp | Leu | Leu | Asp | Thr | Leu | Glu | Asp | Asn | Arg |
| 385 |   |   |   |   | 390 |   |   |   |   | 395 |   |   |   |   | 400 |
| Glu | Trp | Tyr | Gln | Ser | Lys | Ile | Pro | Arg | Ser | Pro | Ser | Asp | Leu | Thr | Asn |
|   |   |   |   | 405 |   |   |   |   | 410 |   |   |   |   | 415 |   |
| Pro | Glu | Arg | Asp | Gly | Pro | Asp | Arg | Phe | Gln | Phe | Glu | Leu | Thr | Leu | Glu |
|   |   |   | 420 |   |   |   |   | 425 |   |   |   |   | 430 |   |   |
| Glu | Ala | Glu | Glu | Glu | Asp | Glu | Glu | Glu | Glu | Glu | Gly | Glu | Glu | Thr |   |
|   |   | 435 |   |   |   |   | 440 |   |   |   |   | 445 |   |   |   |
| Ala | Leu | Ala | Lys | Glu | Ala | Leu | Glu | Leu | Pro | Asp | Thr | Glu | Leu | Leu | Ser |
|   | 450 |   |   |   |   | 455 |   |   |   |   | 460 |   |   |   |   |
| Pro | Glu | Ala | Gly | Pro | Asp | Pro | Gly | Asp | Leu | Pro | Leu | Asp | Asn | Gln | Arg |
| 465 |   |   |   |   | 470 |   |   |   |   | 475 |   |   |   |   | 480 |
| Thr |   |   |   |   |   |   |   |   |   |   |   |   |   |   |   |

( 2 ) INFORMATION FOR SEQ ID NO:3:

( i ) SEQUENCE CHARACTERISTICS:
  ( A ) LENGTH: 506 amino acids
  ( B ) TYPE: amino acid
  ( C ) STRANDEDNESS: single ( D ) TOPOLOGY: linear ( i i ) MOLECULE TYPE: peptide ( x i ) SEQUENCE DESCRIPTION: SEQ ID NO:3:

```
Met Val Pro Leu Asp Glu Leu Asp Trp Cys Leu Asp Gln Leu Glu Thr
 1               5                  10                  15

Leu Gln Thr Arg His Ser Val Gly Glu Met Ala Ser Asn Lys Phe Lys
             20                  25                  30

Arg Ile Leu Asn Arg Glu Leu Thr His Leu Ser Glu Thr Ser Arg Ser
         35                  40                  45

Gly Asn Gln Val Ser Glu Tyr Ile Ser Arg Thr Phe Leu Asp Gln Gln
     50                  55                  60

Thr Glu Val Glu Leu Pro Lys Val Thr Ala Glu Glu Ala Pro Gln Pro
 65                  70                  75                  80

Met Ser Arg Ile Ser Gly Leu His Gly Leu Cys His Ser Ala Ser Leu
                 85                  90                  95

Ser Ser Ala Thr Val Pro Arg Phe Gly Val Gln Thr Asp Gln Glu Glu
             100                 105                 110

Gln Leu Ala Lys Glu Leu Glu Asp Thr Asn Lys Trp Gly Leu Asp Val
         115                 120                 125

Phe Lys Val Ala Glu Leu Ser Gly Asn Arg Pro Leu Thr Ala Ile Ile
     130                 135                 140

Phe Ser Ile Phe Gln Glu Arg Asp Leu Leu Lys Thr Phe Gln Ile Pro
145                 150                 155                 160

Ala Asp Thr Leu Ala Thr Tyr Leu Leu Met Leu Glu Gly His Tyr His
                 165                 170                 175

Ala Asn Val Ala Tyr His Asn Ser Leu His Ala Ala Asp Val Ala Gln
             180                 185                 190

Ser Thr His Val Leu Leu Ala Thr Pro Ala Leu Glu Ala Val Phe Thr
         195                 200                 205

Asp Leu Glu Ile Leu Ala Ala Leu Phe Ala Ser Ala Ile His Asp Val
     210                 215                 220

Asp His Pro Gly Val Ser Asn Gln Phe Leu Ile Asn Thr Asn Ser Glu
225                 230                 235                 240

Leu Ala Leu Met Tyr Asn Asp Ala Ser Val Leu Glu Asn His His Leu
                 245                 250                 255

Ala Val Gly Phe Lys Leu Leu Gln Ala Glu Asn Cys Asp Ile Phe Gln
             260                 265                 270

Asn Leu Ser Ala Lys Gln Arg Leu Ser Leu Arg Arg Met Val Ile Asp
         275                 280                 285

Met Val Leu Ala Thr Asp Met Ser Lys His Met Asn Leu Leu Ala Asp
     290                 295                 300

Leu Lys Thr Met Val Glu Thr Lys Lys Val Thr Ser Leu Gly Val Leu
305                 310                 315                 320

Leu Leu Asp Asn Tyr Ser Asp Arg Ile Gln Val Leu Gln Asn Leu Val
                 325                 330                 335

His Cys Ala Asp Leu Ser Asn Pro Thr Lys Pro Leu Pro Leu Tyr Arg
             340                 345                 350

Gln Trp Thr Asp Arg Ile Met Ala Glu Phe Phe Gln Gln Gly Asp Arg
         355                 360                 365

Glu Arg Glu Ser Gly Leu Asp Ile Ser Pro Met Cys Asp Lys His Thr
     370                 375                 380

Ala Ser Val Glu Lys Ser Gln Val Gly Phe Ile Asp Tyr Ile Ala His
385                 390                 395                 400
```

```
Pro  Leu  Trp  Glu  Thr  Trp  Ala  Asp  Leu  Val  His  Pro  Asp  Ala  Gln  Asp
               405            410                      415

Leu  Leu  Asp  Thr  Leu  Glu  Asp  Asn  Arg  Glu  Trp  Tyr  Gln  Ser  Lys  Ile
               420                 425                      430

Pro  Arg  Ser  Pro  Ser  Asp  Leu  Thr  Asn  Pro  Glu  Arg  Asp  Gly  Pro  Asp
          435                 440                           445

Arg  Phe  Gln  Phe  Glu  Leu  Thr  Leu  Glu  Glu  Ala  Glu  Glu  Glu  Asp  Glu
     450                 455                      460

Glu  Glu  Glu  Glu  Glu  Gly  Glu  Glu  Thr  Ala  Leu  Ala  Lys  Glu  Ala  Leu
465                 470                      475                           480

Glu  Leu  Pro  Asp  Thr  Glu  Leu  Leu  Ser  Pro  Glu  Ala  Gly  Pro  Asp  Pro
               485                      490                      495

Gly  Asp  Leu  Pro  Leu  Asp  Asn  Gln  Arg  Thr
               500                 505
```